United States Patent

Giles et al.

(10) Patent No.: US 6,632,947 B2
(45) Date of Patent: Oct. 14, 2003

(54) PROCESS FOR THE PREPARATION OF SUBSTITUTED THIAZOLIDINEDIONE

(75) Inventors: Robert Gordon Giles, Tonbridge (GB); Norman John Lewis, Tunbridge Wells (GB); Stephen Moore, Lingfield (GB); Colin Ripley Pool, Cranleigh (GB); John Kirby Quick, Crowborough (GB); Michael Urquhart, Southborough (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 10/005,686

(22) Filed: Nov. 8, 2001

(65) Prior Publication Data

US 2002/0042519 A1 Apr. 11, 2002

Related U.S. Application Data

(63) Continuation of application No. 09/367,757, filed as application No. PCT/EP98/00818 on Feb. 13, 1998, now abandoned.

(30) Foreign Application Priority Data

Feb. 18, 1997 (GB) ................................................ 9703310
Feb. 18, 1997 (GB) ................................................ 9703334
Feb. 18, 1997 (GB) ................................................ 9703338

(51) Int. Cl.$^7$ .......................................... C07D 277/04
(52) U.S. Cl. .................................................... 548/183
(58) Field of Search .......................................... 548/183

(56) References Cited

FOREIGN PATENT DOCUMENTS

| EP | 0 454 501 A2 | 10/1991 |
|----|--------------|---------|
| EP | WO 93/13095 | 7/1993 |
| WO | 0 306 228 | 3/1989 |

OTHER PUBLICATIONS

Teruo, et al., "Preparation of thiazolidine–2,4–diones as aldose reductase inhibitors", (1991), Chemical Abstracts, No. 115, No. 17, p. 926, Abstract No. 115:183284f.

*Primary Examiner*—T. A. Solola
(74) *Attorney, Agent, or Firm*—Kathryn L. Sieburth; Mary E. McCarthy; Charles M. Kinzig

(57) ABSTRACT

A process for preparing a compound of formula (I, I) or a tautomeric form thereof or a pharmaceutically acceptable salt thereof or a pharmaceutically acceptable solvate thereof, wherein: J represents O or S; T represents a substituted or unsubstituted aryl group and T$^1$ is O or S; which process comprises reducing a compound of formula (II, II) or a tautomeric form thereof or a salt thereof or a solvate thereof, wherein T and T$^1$ are as defined in relation to formula (I), with a complex hydride reducing agent or a source of a complex hydride reducing agent; and thereafter, as required, preparing a pharmaceutically acceptable salt or a pharmaceutically acceptable solvate of the compound of formula (I) or a tautomeric form thereof.

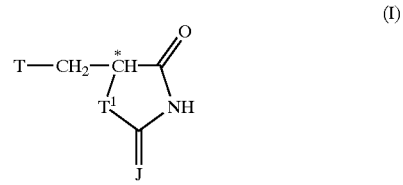

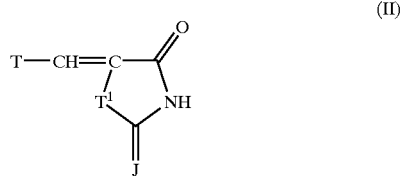

33 Claims, No Drawings

PROCESS FOR THE PREPARATION OF SUBSTITUTED THIAZOLIDINEDIONE

This is a continuation of application Ser. No. 09/367,757 filed Aug. 18, 1999 which is a 35 U.S.C. §371 of National Stage entry of PCT International Application No. PCT/EP98/00818 filed Feb. 13, 1998, now abandoned.

This invention relates to a novel process and in particular to a process for preparing certain substituted thiazolidinedione derivatives and to certain intermediates to the substituted thiazolidinedione derivatives European Patent Application, Publication Number 0306228 discloses certain thiazolidinedione derivatives of formula (A):

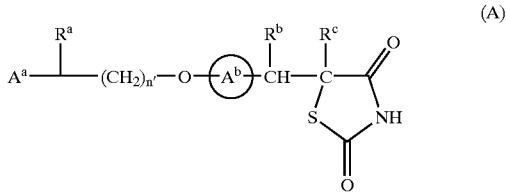

or a tautomeric form thereof or a pharmaceutically acceptable salt thereof, or a pharmaceutically acceptable solvate thereof, wherein:

$A^a$ represents a substituted or unsubstituted aromatic heterocyclyl group;

$R^a$ represents a hydrogen atom, an alkyl group, an acyl group, an aralkyl group, wherein the aryl moiety may be substituted or unsubstituted, or a substituted or unsubstituted aryl group;

$R^b$ and $R^c$ each represent hydrogen or $R^b$ and $R^c$ together represent a bond;

$A^b$ represents a benzene ring having in total up to five substituents; and n' represents an integer in the range of from 2 to 6.

EP 0306228 also discloses a process for reducing the compounds of formula (A) wherein $R^b$ and $R^c$ together represent a bond (the 'benzylidene thiazolidine-2,4-diones') to the corresponding compounds of formula (A) wherein $R^b$ and $R^c$ each represent hydrogen (the 'benzylthiazolidine-2,4-diones'). The particular reduction methods disclosed in EP 0306228 are catalytic hydrogenation methods and dissolving metal reduction methods.

Selective reduction of the exocyclic double bond in the benzylidene thiazolidine-2,4-dione moiety by complex hydride reducing agents is not considered to provide the basis for a viable commercial process due to a general expectation that the required selectivity would not be achieved, with particular reference to the aluminium hydrides, and/or that the reaction would give poor yields. We have now surprisingly discovered that a benzylidene thiazolidine-2,4-dione group is selectively reduced to the corresponding benzyl thiazolidine-2,4-dione, by use of a complex hydride reducing agent in a high yielding and commercially viable process.

Accordingly, the present invention provides a process for preparing a compound of formula (I):

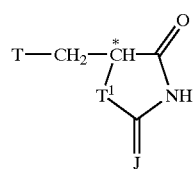

or a tautomeric form thereof or a pharmaceutically acceptable salt thereof or a pharmaceutically acceptable solvate thereof, wherein: J represents O or S; T represents a substituted or unsubstituted aryl group and $T^1$ is O or S; which process comprises, reducing a compound of formula (II):

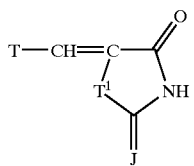

or a tautomeric form thereof or a salt thereof or a solvate thereof, wherein T and $T^1$ are as defined in relation to formula (I), with a complex hydride reducing agent or a source of a complex hydride reducing agent; and thereafter, as required, preparing a pharmaceutically acceptable salt or a pharnaceutically acceptable solvate of the compound of formula (I) or a tautomeric form thereof.

Suitable complex hydride reducing agents include borohydride reducing agents and aluminium hydride reducing agents.

Suitable borohydride reducing agents include diborane and metal borohydrides.

A suitable metal borohydride is an alkali metal borohydride, such as a lithium, sodium or potassium borohydride, especially lithium or potassium.

Borohydrides include unsubstituted and substituted borohydrides.

Suitable substituted borohydrides include borohydrides with up to three substituents on boron selected from such as alkyl and phenyl groups.

Suitable alkyl groups are $C_{1-6}$ alkyl groups, such as ethyl and, especially, butyl groups.

Particular butyl groups are sec and tert butyl groups.

Particular borohydride reducing agents are those which comprise the trihydroborane, triethylborane, tributylborane or triphenylborane moiety.

Favoured borohydride reducing agents include lithium tri-sec-butyl borohydride, potassium tri-sec-butyl borohydride/lithium chloride, soditun tri-sec-butyl borohydride, potassium triphenylborohydride, lithium triethylborohydride, lithium borohydride and sodium borohydride.

One preferred borohydride reducing agent is lithium borohydride.

One preferred borohydride reducing agent is lithium tri-sec-butyl borohydride.

When an unsubstituted metal borohydride is used as the reducing agent, it is preferred if the reduction is carried out in the presence of a base such as pyridine a substituted pyridine, quinoline, a substituted quinoline, a secondary or tertiary amine, such as piperidine or triethylamine, or a phosphine such as triphenylphosphine.

Conveniently, the said base is used as a solvent or co-solvent for the reaction.

A preferred base is pyridine.

A suitable aluminium hydride reducing agent is lithium aluminium hydride.

The reaction conditions for the reduction reaction are the appropriate conditions dictated by the nature of the complex hydride reducing agent chosen:

In one aspect, when the reagent is a borohydride reducing reagent suitable solvents include alkanols, such as methanol and ethanol, tetrahydrofuran and pyridine or mixtures thereof.

When the reducing reagent is an alkali metal borohydride a preferred solvent is pyridine/tetrahydrofuran.

When the reducing reagent is an alkali metal trialkyl or triphenyl borohydride, a preferred solvent is tetrahydrofuran.

The borohydride reduction is carried out at a temperature which provides a suitable rate of formation of the required product, usually at ambient or an elevated temperature, suitably at an elevated temperature, preferably above 50° C., for example 65° C. and conveniently at the reflux temperature of the required solvent. Usually the reactants are mixed at ambient temperature and the reaction mixture is heated at the reflux temperature of the solvent.

In a further aspect, when the reagent is an aluminium hydride reducing reagent, suitable solvents include aprotic solvents such as tetrahydrofuran.

The aluminium hydride reduction is carried out at a temperature which provides a suitable rate of formation of the required product, usually at low to ambient temperature, for example a temperature in the range of from −10 to 10° C., suitably in the range of from −5 to 0° C.

It is considered that the reduction of the compounds of formula (II), wherein $T^1$ is S, especially when the reducing agent is a borohydride reducing agent, proceeds via an intermediate of formula (III):

(III)

or a tautomeric form thereof, or salt thereof, or a solvate thereof, wherein J and T are as defined in relation to formula (I).

The intermediate of formula (III) is obtained in better yield when the reduction is carried out at low temperature. Thus, in a further aspect, the present invention provides a process for preparing a compound of the above defined formula (III), which process comprises, reducing a compound of the above defined formula (II) with a metal hydride reducing agent, preferably a borohydride reducing agent, preferably wherein the reaction is carried at low temperature, suitably below ambient temperature, for example between 0° and 5° C.; and thereafter, as required, preparing a salt or a solvate of the compound of formula (III).

A preferred reducing agent for preparing a compound of formula (III) is lithium or potassium tri-sec-butylborohydride (also known as "L-selectride" or "K-selectride"), preferably lithium tri-sec-butylborohydride.

The present invention further provides a compound of the above defined formula (III) or a tautomeric form thereof, or salt thereof, or a solvate thereof, which compound is useful as an intermediate.

The present invention further comprises a process for converting the above defined compound of formula (III) into the above defined compound of formula (I), which process comprises heating the compound of formula (III), suitably in a solvent, and thereafter as required preparing a pharmaceutically acceptable salt or a pharmaceutically acceptable solvate of the compound of formula (I).

Suitable solvents for the said conversion of the compound of formula (III) into compound (I) include those mentioned above for the preparation of the compound of formula (III).

It will be appreciated from the foregoing discussion that the reduction of the compound of formula (II) to provide a compound of formula (I), especially when employing borohydride reducing agents, is preferably carried out at a temperature high enough to ensure conversion of the intermediate of formula (III) into the compound of formula (I), suitably the temperature is above 50° C., for example 65° C. and conveniently the reflux temperature of the reaction solvent.

Suitable general reaction conditions for the borohydride and aluminium hydride reductions are also as described in "Reductions by the Alumino- and Borohydrides in Organic Synthesis" by J. Seyden-Penne (VCH Publishers, Inc./Lavoisier—Tec & Doc, published 1991) and the references disclosed therein.

The compounds of formula (I) (or (III)) are isolated from the reaction and subsequently purified by use of conventional isolation and purification methods such as chromatography and crystallization/recrystalliazation.

The complex hydride reducing agents of the process are usually commercially available or they can be prepared using conventional procedures, for example the borohydride and aluminium hydride reagents can be prepared using methods such as those described in "Reductions by the Alumino- and Borohydrides in Organic Synthesis" (ibid) and particularly in the references cited therein.

Certain of the borohydride reducing agents are conveniently prepared in situ. For example, lithium tri-sec-butyl borohydride is conveniently prepared from tri-sec-butyl borane and lithium aluminium hydride.

Also, lithium borohydride is conveniently prepared from sodium borohydride and a lithium salt according to known procedures such as those disclosed in Inorg. Chem. 1981, 20, 4454; J. Am. Chem. Soc. 1953, 75, 209; Nature 1954, 173, 125 and J. Am. Chem. Soc. 1955, 77, 6209.

Suitably T represents a moiety selected from the list consisting of (Ia), (Ib), (Ic), (Id), (Ie), (If), (Ig), (Ih), (Ii), (Ij), (Ik), (Il), (Im), (In), (Io), (Ip) and (Iq):

(Ia)

$$A^1-\overset{R^1}{\underset{}{N}}-(CH_2)_n-O-(A^2)-$$

wherein $A^1$, $A^2$, $R^1$ and n are as defined in relation to formula (I) of EP 0306228;

(Ib)

$$L^2-\overset{L^1}{\underset{L^3}{C}}-R^2-O-\text{(phenyl)}-$$

wherein $R^2$, $L^1$, $L^2$ and $L^3$ are as defined in relation to formula (I) of EP 0008203;

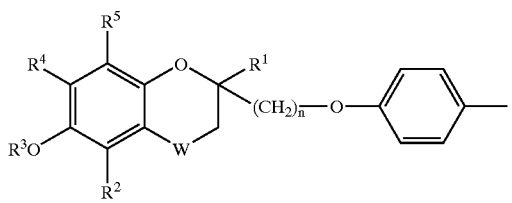
(Ic)

wherein R¹, R², R³, R⁴, R⁵, W and n are as defined in relation to formula (I) of EP(0139421;

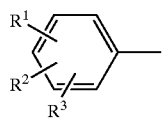
(Id)

wherein R¹, R² and R³ are as defined in relation to formula (I) of EP 0032128;

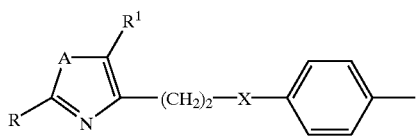
(Ie)

wherein A, R, R¹ and X are as defined in relation to formula (I) of EP 0428312;

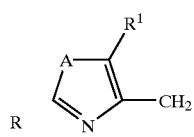
(If)

when A, B, R and R¹ are as defined in relation to formula (II) of EP 0428312;

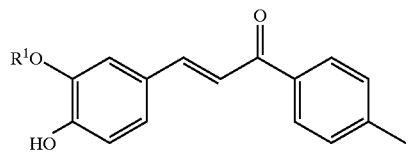
(Ig)

wherein R¹ is as defined in relation to formula (I) of EP 0489663;

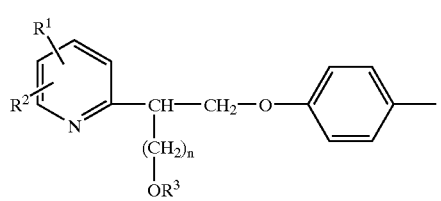
(Ih)

wherein R¹, R², R³ and n are as defined in relation to formula (I) of EP 0155845;

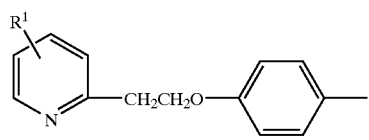
(Ii)

when R¹ is as defined in relation to formula (I) of EP 0257781;

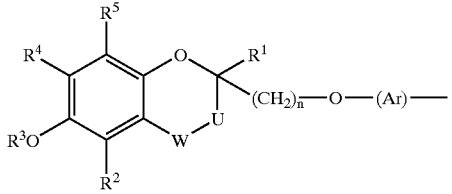
(Ij)

wherein Ar, R¹, R², R³, R⁴, R⁵, n, U and W are as defined in relation to formula (I) of U.S. Pat. No. 5104888;

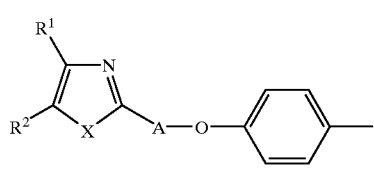
(Ik)

when A, R¹, R² and X are as defined in relation to formula (I) of EP 0208420;

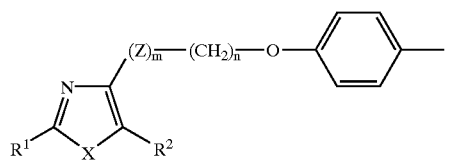
(Il)

when R¹, R², X, Z m and n are as defined in relation to formula (I) of EP 0177353;

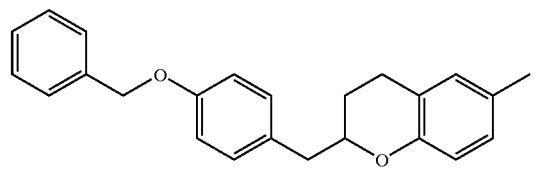
(Im)

according to formula (I) of EP 0319189;

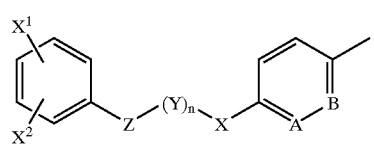
(In)

wherein A, B, X, X¹, X², n and Z are as defined in relation to formula (I) of EP 0332331;

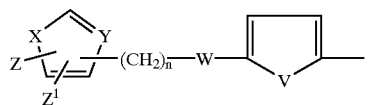
(Io)

wherein V, W, X, Y, Z, Z$^1$ and n are as defined in EP 0332332; and

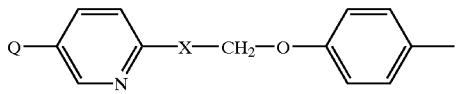
(Ip)

wherein Q and X are as defined in relation to formula (I) of International Application No. WO 92/18501.

Favourably, T represents a moiety of the above defined formula (Ia), (Ic), (Ie), (If), (Ii), (Ik) or (Io).

In particular T represents a moiety selected from the list consisting of (a), (b), (c), (d), (e), (f), (g), (h) (i) and (j):

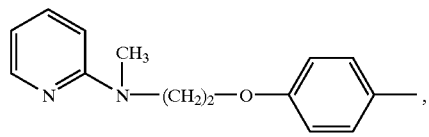
(a)

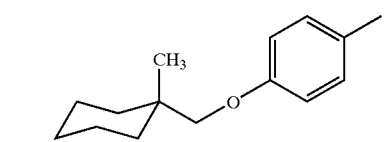
(b)

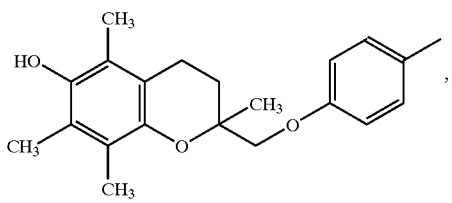
(c)

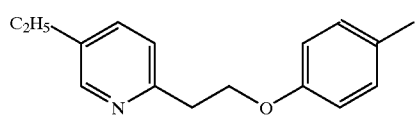
(d)

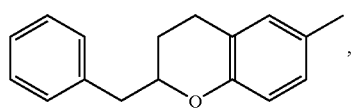
(e)

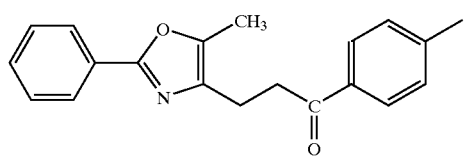
(f)

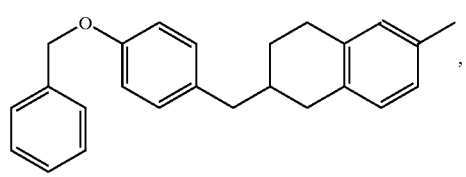
(g)

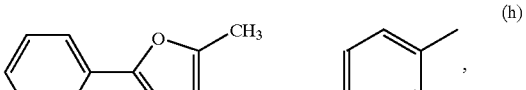
(h)

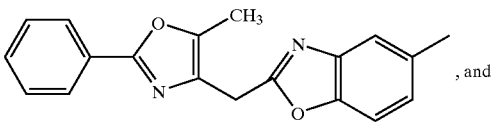
, and
(i)

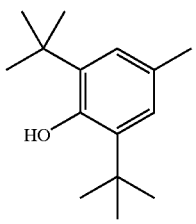
(j)

Preferably, T represents a moiety of the above defined formula (Ia).

Preferably, T$^1$ represents S.

Preferably J represents O.

Thus, in a preferred aspect, the invention provides a process for preparing a compound of formula (I) as defined in EP 0306228: Accordingly, the invention provides a process for preparing a compound of formula (IA):

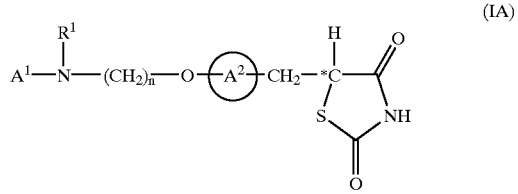
(IA)

or a tautomeric form thereof or a pharmaceutically acceptable salt thereof, or a pharmaceutically acceptable solvate thereof, wherein:

A$^1$ represents a substituted or unsubstituted aromatic heterocyclyl group;

R$^1$ represents a hydrogen atom, an alkyl group, an acyl group, an aralkyl group, wherein the aryl moiety may be substituted or unsubstituted, or a substituted or unsubstituted aryl group;

A$^2$ represents a benzene ring having in total up to five substituents; and n represents an integer in the range of from 2 to 6; which process comprises, treating a compound of formula (IIB):

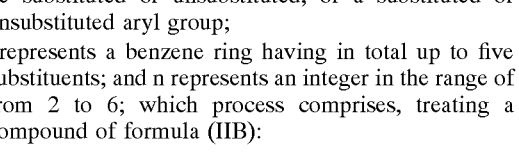
(IIB)

or a tautomeric form thereof or a salt thereof, or a solvate thereof, wherein A$^1$, A$^2$, R$^1$ and n are as defined in relation to formula (IA) with a complex hydride reducing agent or a source of a complex hydride reducing agent, such as a borohydride reducing agent or a source of a borohydride reducing agent; and thereafter, as required, preparing a pharmaceutically acceptable salt, or a pharmaceutically acceptable solvate of the compound of formula (IA) or a tautomeric form thereof.

In a preferred aspect, the compound of formula (HII) is a compound of formula (IIIA):

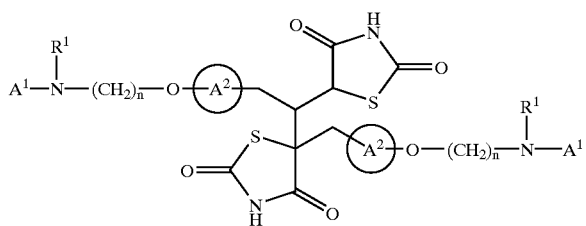

wherein $A^1, A^2, R^1$ and n are as defined in relation to formula (IA) herein.

Unless mentioned to the contrary herein, the suitable, apt, favoured and preferred values for each variable in the above mentioned moieties of formula (Ia), (Ib), (Ic), (Id), (Ie), (If), (Ig), (Ih), (Ii), (Ij), (Ik), (Il), (Im), (In), (Io) or (Ip) are as defined in the European and International patent applications or United States patents mentioned above in respect of each of the said formulae.

In particular, the suitable, apt, favoured and preferred values of the variables $A^1$, $A^2$, $R^1$ and n in formulae (IA), (IIB) and (IIIA) are as defined in relation to formula (I) of EP 0306228.

A most preferred value of $A^1$ in formulae (IA), (IIB) and (IIIA) is a 2-pyridyl group.

A most preferred value of $A^2$ in formulae (IA), (IIB) and (IIIA) is a moiety of formula:

A most preferred value of $R^1$ in formulae (IA), (IIB) and (IIIA) is a methyl group.

A most preferred value of n in formulae (IA), (IIB) and (IIIA) is 2.

Most favourably, T represents a moiety of the above defined formula (a), (c) or (d).

A preferred value of T is a moiety of the above defined formula (a).

A most preferred value of formula (IA) is 5-{4-[2-(N-methyl-N-(2-pyridyl)amino)ethoxy]benzyl}-2,4-thiazolidinedione, or a tautomeric form thereof or a salt thereof, or a solvate thereof.

A most preferred value of formula (IIB) is 5-{4-[2-(N-methyl-N-(2-pyridyl)amino)ethoxy]benzylidene}-2,4-thiazolidinedione or a tautomeric form thereof or a salt thereof, or a solvate thereof.

When the reaction comprises a compound of formula (IIB) as substrate it is preferred if the reaction is carried out at an elevated temperature, preferably above 50° C., for example at 65° C.

A preferred example of a compound of formula (IIIB) is 5-{4-[2-(N-methyl-N-(2-pyridyl)amino)ethoxy]benzyl}-5-{1-[2,4-dioxothiazolidin-5-yl]-1-[4-(2-(N-methyl-N-(2-pyridyl)amino)ethoxy)phenyl]methyl}-2,4 thiazolidinedione.

Suitable salts are pharmaceutically acceptable salts.

Suitable solvates are pharmaceutically acceptable solvates.

Unless mentioned to the contrary herein, the suitable, apt, favoured and preferred pharmaceutically acceptable salts, pharmaceutically acceptable solvates and tautomeric forms of each of the compounds in the above mentioned moieties of formula (Ia), (Ib), (Ic), (Id), (Ie), (If), (Ig), (Ih), (Ii), (Ij), (Ik), (Il), (Im), (In), (Io) or (Ip) are as defined in the European or International patent applications or United States patents mentioned above in respect of each of the said formulae.

In particular it should be mentioned that suitable pharmaceutically acceptable salts include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

In addition should be mentioned those pharmaceutically acceptable salts provided by pharmaceutically acceptable acids including mineral acids, for example for compounds of formula (I) wherein T represents a moiety of formula (Ia) suitable salts are those disclosed in WO 94/05659 including salts provided by mineral acids, such as hydrobromic, hydrochloric and sulphuric acids, and organic acids, such as methanesulphonic, tartaric and maleic acids, especially tartaric and maleic acid.

The compounds of formula (II) may be prepared according to known methods, for example by use of the appropriate method disclosed in the abovementioned European and International patent applications or United States patents. The contents of the abovementioned European and International patent applications and United States patents are incorporated herein by reference.

In particular compounds of formula (IIB) may be prepared according to the methods disclosed in EP 0306228.

The following examples illustrate the invention but do not limit it in any way.

EXAMPLE 1

Preparation of 5-{4-[2-(N-methyl-N-(2-pyridyl)amino)ethoxy]benzyl}-2,4-thiazolidinedione (IA) via reduction of 5-{4-[2-(N-methyl-N-(2-pyridyl)amino)ethoxy]benzylidene}2,4-thiazolidinedione (IIB)

(a) Using lithium tri-sec-butyl borohydride.

A 1M solution of lithium tri-sec-butyl borohydride in tetrahydrofuran (220 ml, 0.22 moles) was added to a suspension of IIB (35.5 g, 0.1 moles) in tetrahydrofliran (310 ml) at 25° C. over 30 minutes. The resulting mixture was heated and held at reflux temperature for two and a half hours, and then cooled to 5° C. An aqueous solution of sodium hydroxide (10% w/v, 100 ml, 0.25 moles) was added, followed by 27% aqueous hydrogen peroxide solution (50 ml, 0.4 moles). The resultant solution was stirred at 25° C. for three hours, diluted with water (100 ml), and then concentrated via vacuum distillation until a residual volume of 300 ml was achieved. Hydrochloric acid (2.5 M, approx. 200 ml) was added to the rapidly stirred mixture at 20 to 25°

C. and the resulting precipitate was filtered, washed with water, and dried at 50 dec C. in vacuo, to give (IA) (34.4 g). The crude product was recrystallised from 99% IMS (20 ml per g of crude (IA) giving a 79% overall yield.

(b) Using lithium borohydride.

A solution of lithium borohydride (67.5 g, 3.1 mole) in tetrahydrofuran (1.54L) was added via cannular to a stirred suspension of (IIB) (500 g, 1.4 mol) in tetrahydrofuran (950 ml) and pyridine (1.13 L) at room temperature under nitrogen over 1.5 hours. The mixture was heated to reflux, stirred for 3 hours and cooled to room temperature. The stirred reaction mixture was quenched into hydrochloric acid (670 ml) and water (4.4 L) at 8° C. over 0.67 hours using tetrahydrofuran (250 ml) to wash out residual material. The quench mixture was stirred at 26° C. for 0.25 hours, heated to reflux and stirred for 0.75 hours. The hot mixture was allowed to stand for 0.17 hours, filtered through celite, the residue was pulled to dryness and washed with water (500 ml). The aqueous washings were added to the filtrate and stirred at room temperature for 14 hours. The precipitated product was collected by filtration under vacuo, pulled to dryness, washed with water (2.8 L) and pulled dry. The damp solid was washed with industrial methylated spirit (2×500 ml), and dried at 45° C. for 72 hours to give (IA) (386.5 g, 77%).

c) Using sodium borohydride and lithium chloride, (in-situ preparation of lithium A solution of sodium borohydride (0.24 g, 6.34 mmole) in pyridine (5 ml) was stirred at 25° C. under nitrogen for 0.25 hours then heated to 65° C. under reflux. A solution of lithium chloride (0.40 g, 9.44 mmole) in pyridine (5 ml) was added dropwise via cannular to the stirred mixture at 65° C. which was then held at this temperature for 2 hours, diluted with tetrahydrofiran (20 ml) and heated at reflux for a further 0.5 hours. The mixture was cooled to 30° C., (IIB) (1.0 g, 2.82 mmole) was added in portions and the reaction mixture was heated to reflux for 4 hours. A solution of hydrochloric acid (1 ml) and water (10 ml) was added dropwise to the reaction mixture at 5° C. The mixture was concentrated in vacuo, pyridine (4 ml) and water (6 ml) were added and the mixture was stirred at 5° C. with the pH being adjusted to 6 using hydrochloric acid. Water (10 ml) was added and the mixture was stirred for 15 hours. The suspension was filtered, the residue was washed with water (10 ml), pulled dry and dried at 50° C. for 24 h to give (IA), (0.88 g, 88%).

EXAMPLE 2

Preparation of 5-{4-[2-(N-methyl-N-(2-pyridyl) amino)ethoxy]benzyl}-2,4-thiazolidinedione (IA) via reduction of 5-{4-[2-(N-methyl-N-(2-pyridyl) amino)ethoxy]benzylidene}2,4-thiazolidinedione (IIB), using lithium aluminium hydride To a suspension of lithium aluminium hydride (1.13 g, 1 mole equivalent) in tetrahydrofuran (200 ml) at 0° C. was added (IIB) (10 g, 1 mole equivalent) in portions over 15 minutes. The temperature was kept below 5° C. during the addition. The mixture was stirred at 0° C. for 30 minutes, and then at 10° C. until the reaction was judged to be complete by HPLC (1.75 hours). The solution yield of (IA) was 69%.

EXAMPLE 3

Preparation of 5-{4-[2-(N-methyl-N-(2-pyridyl) amino)ethoxy]benzyl}-5-{1-[2,4-dioxothiazolidin-5-yl]-1-[4-(2-(N-methyl-N-(2-pyridyl)amino)ethoxy) phenyl]methyl}-2,4-thiazolidinedione (IIIA) from 5-{4-[2-(N-methyl-N-(2-pyridyl)amino)ethoxy] benzylidene}2,4-thiazolidinedione (IIB)

To a solution of compound (IIB) (3.56 g) in tetrahydrofuran (THF, 120 ml) at −5 to 0° C. was added a 1 M solution of lithium tri-sec-butylborohydride (L-selectride) in THF (22 ml). The resulting mixture was stirred for 40 minutes, and then cooled to −10° C. to stop the reaction. Sodium hydroxide solution (10% w/w, 40 ml) was carefully added, followed by aqueous hydrogen peroxide (27% w/w, 10 ml) to ensure destruction of the borohydride reagent. THF was removed in vacuo, and the aqueous mixture was neutralised to pH 7 using 2M hydrochloric acid. The resulting solid was filtered and discarded, and the filtrate was cooled to 4° C. After standing overnight a second crop of solid was obtained and this was purified twice by flash column chromatography using dichloromethane/methanol as eluent. Compound (IIIC)was isolated as white crystals (109 mg, 3% isolated yield).

EXAMPLE 4

Preparation of 5-{4-[2-(5-ethyl-2-pyridyl)ethoxy] benzyl}-2,4-thiazolidine-2,4-dione (ID) via reduction of 5-{4-[2-(5-ethyl-2-pyridyl)ethoxy] benzilidene}-2,4-thiazolidine-2,4-dione (IID)

A 2.0 M solution of lithium borohydride in tetrahydrofuran (31 ml, 62.0 mmol) was added dropwise to a stirred suspension of 5-{4-[2-(5-ethyl-2-pyridyl)ethoxy] benzilidene}-2,4-thiazolidine-2,4-dione (10.0 g, 28.22 mmol) in tetrahydrofuran (19 ml) and pyridine (23 ml) at 30° C. under nitrogen. The resulting mixture was heated under reflux for 4 h (reaction monitored by HPLC) and then cooled to ambient temperature and added dropwise to an efficiently stirred solution of conc. hydrochloric acid (13.5 ml) in water (88.7 ml) between 10° C. and 20° C. The resulting orange suspension was heated to reflux temperature and held for 30 minutes and then cooled to ambient temperature. The resulting suspension was stirred for 30 minutes and the product was collected by filtration and washed with water (20 ml×3). The crude product was heated to reflux in acetic acid (50 ml) and charcoal was added (1.5 g) to the resulting solution, which was then diluted with ethanol (50 ml), filtered through celite, and the celite bed washed through with hot ethanol (50 ml). The filtrate and washings were combined and allowed to cool to 5° C. resulting in crystallisation of a white solid which was isolated by filtration to give compound (ID) (5.29 g, 53%). A second crop of material was obtained by partial concentration of the mother liquor (0.81 g, 8.1%).

What is claimed is:

1. A process, for preparing a compound of formula (IA):

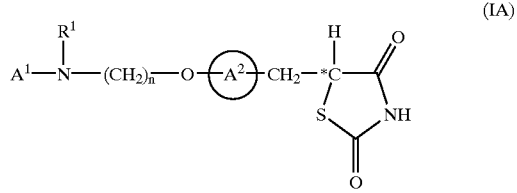

or a tautomeric form thereof or a pharmaceutically acceptable salt thereof, or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6;
which process comprises treating a compound of formula (IIB):

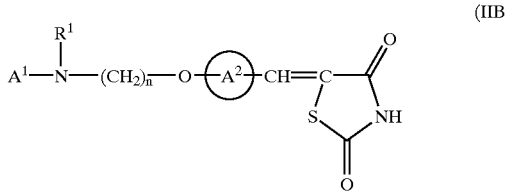 (IIB)

or a tautomeric form thereof or a salt thereof, or a solvate thereof, wherein $A^1$, $A^2$, $R^1$ and n are as defined in relation to formula (IA) with a complex hydride reducing agent or a source of a complex hydride reducing agent.

2. A process according to claim 1, wherein (IA) is 5-{4-[2-(N-methyl-N-2-pyridyl)amino)ethoxy]benzyl}-2,4-thiazolidinedione, or a tautomeric form thereof or a salt thereof, or a solvate thereof and (IIB) is 5-{4-[2-(N-methyl-N-(2-pyridyl)amino)ethoxy]benzylidene}-2,4-thiazolidinedione or a tautomeric form thereof or a salt thereof, or a solvate thereof.

3. A process of claim 1 further comprising the step of preparing a pharmaceutically acceptable salt or pharmaceutically acceptable solvate of the compound of formula (IA) or a tautomeric form thereof.

4. A process for preparing a compound which is 5-{4-[2-(N-methyl-N-(2-pyridyl)amino)ethoxy]benzyl}-2,4-thiazolidinedione, or a tautomeric form thereof, or a pharmaceutically acceptable salt thereof or a pharmaceutically acceptable solvate thereof, comprising
reducing 5-{4-[2-(N-methyl-N-(2-pyridyl)amino)ethoxy]benzylidene}-2,4-thiazolidinedione, or a tautomeric form thereof, or a salt thereof or a solvate thereof with a complex hydride reducing agent selected from borohydride reducing agents and aluminium hydride reducing agents, and
thereafter optionally forming a pharmaceutically acceptable salt, or a pharmaceutically acceptable solvate of 5-{4-[2-(N-methyl-N-(2-pyridyl)amino)ethoxy]benzyl}-2,4-thiazolidinedione, or a tautomeric form thereof.

5. The process of claim 4, wherein the complex reducing agent comprises a borohydride reducing agent.

6. The process of claim 5, wherein the borohydride reducing agent comprises a diborane or a metal borohydride.

7. The process of claim 6, wherein the borohydride reducing agent comprises an alkali metal borohydride.

8. The process of claim 7, wherein the alkali metal borohydride is a lithium or a potassium borohydride.

9. The process of claim 5, wherein the borohydride reducing agent comprises a metal borohydride which is unsubstituted or substituted with up to three substituents selected from alkyl and phenyl.

10. The process of claim 5, wherein the borohydride reducing agent is selected from the group consisting of lithium tri-sec-butyl borohydride, potassium tri-sec-butyl borohydride, sodium tri-sec-butyl borohydride, potassium triphenylborohydride, lithium triethylborohydride, lithium borohydride, and sodium borohydride.

11. The process of claim 10, wherein the borohydride reducing agent is selected from the group consisting of lithium tri-sec-butyl borohydride and lithium borohydride.

12. The process of claim 4, wherein the borohydride reducing agent is prepared in situ.

13. The process of claim 4, wherein the complex reducing agent comprises an aluminium hydride reducing agent.

14. The process of claim 13, wherein the aluminium hydride reducing agent comprises lithium aluminium hydride.

15. The process of claim 9 wherein the metal borohydride is unsubstituted and the reduction reaction is carried out in the presence of a base.

16. The process of claim 15 wherein the base is selected from the group consisting of pyridine, substituted pyridines, quinoline, substituted quinolines, secondary amines, tertiary amine, and phosphines.

17. The process of claim 16 wherein the base is pyridine.

18. The process of claim 4, wherein 5-{4-[2-(N-methyl-N-(2-pyridyl)amino)ethoxy]benzylidene}-2,4-thiazolidinedione, or a tautomeric form thereof is reduced.

19. The process of claim 4, wherein a salt of 5-{4-[2-(N-methyl-N-(2-pyridyl)amino)ethoxy]benzylidene}-2,4-thiazolidinedione, or a tautomeric form thereof is reduced.

20. The process of claim 19, wherein a mineral acid salt of 5-{4-[2-(N-methyl-N-(2-pyridyl)amino)ethoxy]benzylidene}-2,4-thiazolidinedione, or a tautomeric form thereof is reduced.

21. The process of claim 20, wherein the mineral acid is hydrobromic acid, hydrochloric acid, or sulphuric acid.

22. The process of claim 19, wherein an organic acid salt of 5-{4-[2-(N-methyl-N-(2-pyridyl)amino)ethoxy]benzylidene}-2,4-thiazolidinedione, or a tautomeric form thereof is reduced.

23. The process of claim 22 wherein the organic acid is methanesulphonic acid or tartaric acid.

24. The compound which is 5-{4-[2-(N-methyl-N-(2-pyridyl)amino)ethoxy]benzyl}-2,4-thiazolidinedione, a pharmaceutically acceptable salt thereof and/or a pharmaceutically acceptable solvate thereof, or a tautomeric form thereof, produced by the process of claim 4.

25. The process of claim 24, wherein the 5-{4-[2-(N-methyl-N-(2-pyridyl)amino)ethoxy]benzyl}-2,4-thiazolidinedione is in the form of a pharmaceutically acceptable salt.

26. The compound of claim 25, wherein the pharmaceutically acceptable salt is a metal salt selected from aluminium salts, alkali metal salts and alkaline earth metal salts.

27. The compound of claim 26, wherein the metal salt is sodium, potassium, calcium or magnesium salt.

28. The compound of claim 25, wherein the pharmaceutically acceptable salt is an ammonium or substituted ammonium salt.

29. The compound of claim 25, wherein the pharmaceutically acceptable salt is a mineral acid salt.

30. The compound of claim 29, wherein the mineral acid is hydrobromic acid, hydrochloric acid, or sulphuric acid.

31. The compound of claim 25, wherein the pharmaceutically acceptable salt is an organic acid salt.

32. The compound of claim 31, wherein the organic acid is methanesulphonic acid, tartaric acid, or maleic acid.

33. The compound of claim 32, wherein the organic acid is maleic or tartaric acid.

* * * * *

UNITED STATES PATENT AND TRADEMARK OFFICE
CERTIFICATE OF CORRECTION

PATENT NO.    : 6,632,947 B2
DATED         : October 14, 2003
INVENTOR(S)   : Giles et al.

It is certified that error appears in the above-identified patent and that said Letters Patent is hereby corrected as shown below:

Title page,
Item [56], References Cited, FOREIGN PATENT DOCUMENTS, please delete "WO 0 306 228" and replace it with -- "EP 0 306 228".
Item [57], ABSTRACT,
Line 1, please delete "compound of formula (l, l)" and replace it with -- "compound of formula (l)...".
Line 6, please delete "compound of formula (ll, ll)" and replace it with -- "compound of formula (ll)...".

Column 2,
Line 52, please delete "soditun" and replace it with -- sodium --.

Column 9,
Line 5, please delete "(Hll)" and replace it with -- (lll)... --.
Line 62, please delete "(lllB)" and replace it with -- (lllA)... --.

Column 10,
Line 57, please delete "tetrahydrofliran" and replace it with -- tetrahydrofuran... --.

Column 11,
Line 26, please add -- borohydride -- after the word lithium.

Column 12,
Line 13, please delete "(lllC)" and replace it with -- (lllA)... --.

UNITED STATES PATENT AND TRADEMARK OFFICE
CERTIFICATE OF CORRECTION

PATENT NO. : 6,632,947 B2
DATED : October 14, 2003
INVENTOR(S) : Giles et al.

It is certified that error appears in the above-identified patent and that said Letters Patent is hereby corrected as shown below:

Column 14,
Line 40, please delete " process" and replace it with -- compound... --.

Signed and Sealed this

Thirty-first Day of August, 2004

JON W. DUDAS
*Director of the United States Patent and Trademark Office*